United States Patent
Lee et al.

(10) Patent No.: US 10,265,456 B2
(45) Date of Patent: Apr. 23, 2019

(54) BLOOD FILTER AND METHOD OF MANUFACTURING THE SAME

(71) Applicant: KOLON INDUSTRIES, INC., Gwacheon-si, Gyeonggi-do (KR)

(72) Inventors: Min Ho Lee, Yongin-si (KR); Jin Il Kim, Yongin-si (KR)

(73) Assignee: KOLON INDUSTRIES, INC., Gwacheon-si, Gyeonggi-do (KR)

( * ) Notice: Subject to any disclaimer, the term of this patent is extended or adjusted under 35 U.S.C. 154(b) by 30 days.

(21) Appl. No.: 15/540,817

(22) PCT Filed: Dec. 28, 2015

(86) PCT No.: PCT/KR2015/014335
§ 371 (c)(1),
(2) Date: Jun. 29, 2017

(87) PCT Pub. No.: WO2016/108543
PCT Pub. Date: Jul. 7, 2016

(65) Prior Publication Data
US 2017/0354774 A1 Dec. 14, 2017

(30) Foreign Application Priority Data
Dec. 30, 2014 (KR) .......... 10-2014-0193439

(51) Int. Cl.
*A61M 1/02* (2006.01)
*A61M 1/34* (2006.01)
(Continued)

(52) U.S. Cl.
CPC ............ *A61M 1/3403* (2014.02); *A61M 1/02* (2013.01); *A61M 1/34* (2013.01); *A61M 1/3406* (2014.02);
(Continued)

(58) Field of Classification Search
None
See application file for complete search history.

(56) References Cited

U.S. PATENT DOCUMENTS 5,298,165 A * 3/1994 Oka .................. A61M 1/34
210/335
5,582,907 A 12/1996 Pall
(Continued)

FOREIGN PATENT DOCUMENTS

EP 1582228 A1 10/2005
JP 2003-320026 A 11/2003
(Continued)

OTHER PUBLICATIONS

ASTM F 316-03, Standard Test Methods for Pore Size Characteristics of Membrane Filters by Bubble Point and Mean Flow Pore Test, ASTM International (Year: 2006).*

*Primary Examiner* — Chester T Barry
(74) *Attorney, Agent, or Firm* — Novick, Kim & Lee, PLLC; Jae Youn Kim

(57) ABSTRACT

Disclosed are a blood filter which exhibits excellent leukocyte elimination performance as well as significantly improved blood throughput per unit time and erythrocyte recovery rate and a method of manufacturing the same. The blood filter of the present invention includes a pre-treatment filter which is a laminate of first non-woven fabrics having a mean fiber diameter of 5 to 30 μm and a mean pore size of 10 to 30 μm, and a main filter which is a laminate of second non-woven fabrics having a mean fiber diameter of 1 to 5 μm, a mean pore size of 5 to 10 μm and a mean pore size distribution rate of 30% or more. A filling density of the pre-treatment filter and a filling density of the main filter, with respect to a target blood throughput of the blood filter, are 0.1 g/100 ml to 1 g/100 ml and 1 g/100 ml to 3 g/100 ml, respectively.

3 Claims, 1 Drawing Sheet

(51) Int. Cl.
*A61M 1/38* (2006.01)
*D01D 1/04* (2006.01)
*D01D 5/08* (2006.01)
*D01D 7/00* (2006.01)
*D01F 6/62* (2006.01)
*B01D 39/16* (2006.01)
*B01D 71/48* (2006.01)
*B01D 39/20* (2006.01)
*B01D 63/08* (2006.01)

(52) U.S. Cl.
CPC ........ *A61M 1/3482* (2014.02); *A61M 1/3496* (2013.01); *A61M 1/382* (2013.01); *B01D 39/1623* (2013.01); *B01D 39/201* (2013.01); *B01D 71/48* (2013.01); *D01D 1/04* (2013.01); *D01D 5/08* (2013.01); *D01D 7/00* (2013.01); *D01F 6/62* (2013.01); *A61M 2207/00* (2013.01); *B01D 63/08* (2013.01); *B01D 2239/0421* (2013.01); *B01D 2239/0492* (2013.01); *B01D 2239/06* (2013.01); *B01D 2239/0622* (2013.01); *B01D 2239/10* (2013.01); *B01D 2239/1216* (2013.01); *B01D 2239/1233* (2013.01)

(56) References Cited

U.S. PATENT DOCUMENTS

| | | | | |
|---|---|---|---|---|
| 2012/0322046 | A1* | 12/2012 | Miyazaki | G01N 15/1463 435/2 |
| 2013/0277297 | A1* | 10/2013 | Suzuki | A61M 1/3633 210/257.1 |

FOREIGN PATENT DOCUMENTS

| | | |
|---|---|---|
| JP | 2004-215873 A | 8/2004 |
| JP | 2009263818 A | 11/2009 |
| JP | 2012183237 A | 9/2012 |
| KR | 10-2007-0095388 A | 9/2007 |
| KR | 10-2012-0105648 A | 9/2012 |
| KR | 10-2014-0004110 A | 1/2014 |
| KR | 20140004277 A | 1/2014 |
| KR | 10-1441165 B1 | 9/2014 |

\* cited by examiner

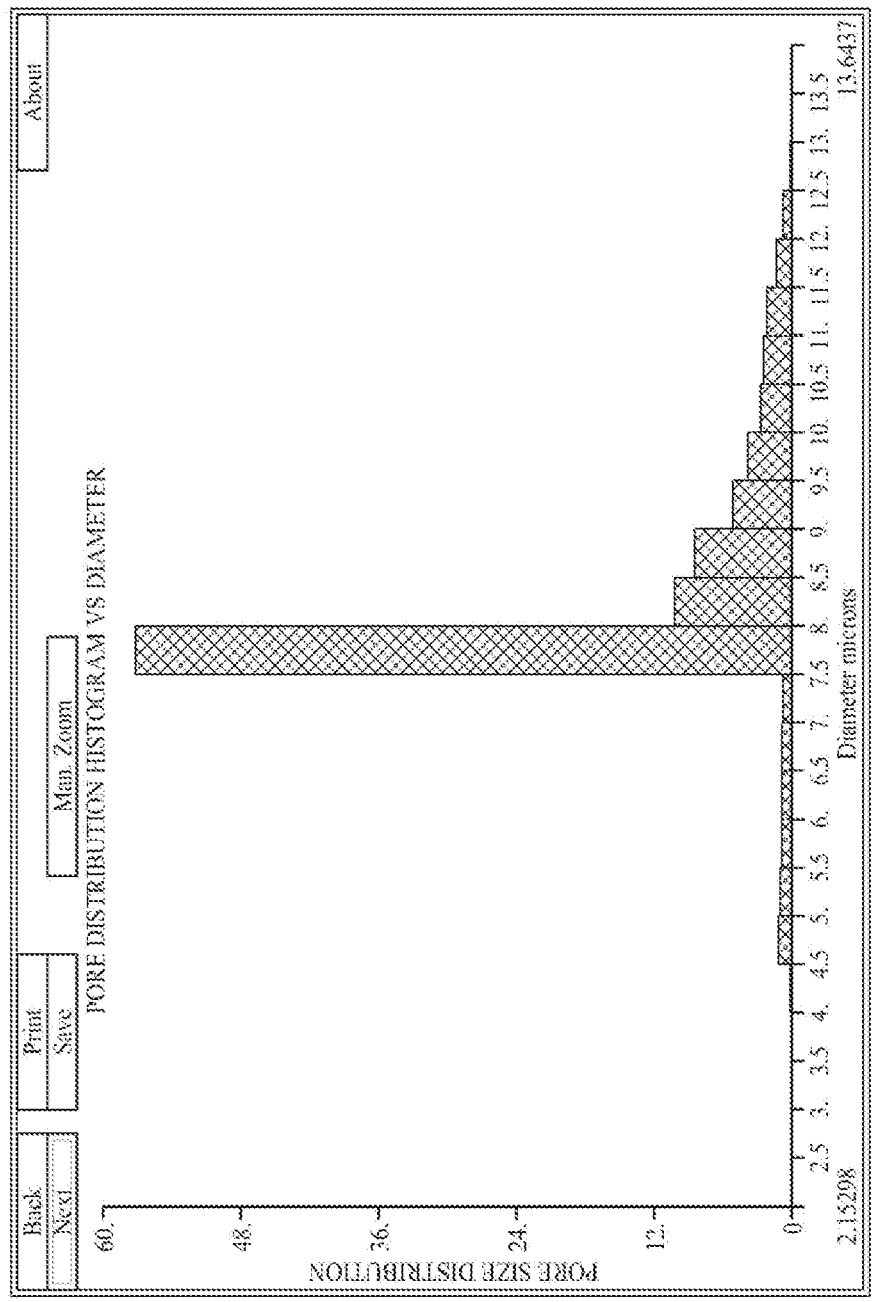

BLOOD FILTER AND METHOD OF MANUFACTURING THE SAME

TECHNICAL FIELD

The present invention relates to a blood filter and a method of manufacturing the same, and more particularly, the present invention relates to a blood filter which exhibits excellent leukocyte elimination performance as well as significantly improved blood throughput per unit time and erythrocyte recovery rates and a method of manufacturing the same.

BACKGROUND ART

Transfusion of leukocyte-containing blood or erythrocyte concentration preparations may cause side effects such as headache, vomiting, chills, fever, viral infection, and allogeneic antigen sensitization. To prevent these side-effects, it is necessary to remove leukocytes present in blood of subjects who receive a transfusion.

Methods of removing leukocytes from blood include a centrifugation method which separates leukocytes by rotating blood at a high rate, a filter method which separates leukocytes by allowing blood to pass through a filter to adsorb leukocytes on the filter, and a dextran method which includes adding dextran to blood, stirring the mixture and then removing a separated leukocyte layer by suction. Thereamong, the filter method which exhibits excellent leukocyte separation performance, is easy to handle and is inexpensive is widely used.

Such a blood filter should satisfy a variety of requirements. First, the blood filter should treat a large amount of blood within a short time to prevent blood coagulation. Second, the blood filter should have a high leukocyte removal rate to prevent the aforementioned side-effects. Third, the blood filter should allow other beneficial ingredients in blood, for example, erythrocytes, to pass therethrough without causing damage to the ingredients.

In Korean Patent No. 1441165, the present applicant disclosed a blood filter which has an increased blood throughput per unit time as well as improved leukocyte elimination performance and erythrocyte recovery rates by imparting excellent blood affinity to a melt-blown non-woven fabric.

However, the melt-blown non-woven fabric, which is a porous material, has a low pore size uniformity. For this reason, a plurality of porous materials need to be laminated to improve leukocyte elimination performance. As a result, there are limitations on increasing blood throughput per unit time, improving erythrocyte recovery rates and reducing erythrocyte damage rates.

DISCLOSURE

Technical Problem

Therefore, the present invention relates to a blood filter and a method of manufacturing the same to prevent problems resulting from limitations and drawbacks of the related art, and it is one object of the present invention to provide.

It is one object of the present invention to provide a blood filter which exhibits excellent leukocyte elimination performance as well as significantly improved blood throughput per unit time and erythrocyte recovery rates.

It is another object of the present invention to provide a method of manufacturing a blood filter which exhibits excellent leukocyte elimination performance as well as significantly improved blood throughput per unit time and erythrocyte recovery rates.

Other features and advantages of the present invention will be described in the following and would partially be obvious from such description. Alternatively, other features and advantages of the present invention could be understood through implementation of the present invention.

Technical Solution

In accordance with the present invention, the above and other objects can be accomplished by the provision of a blood filter including a pre-treatment filter for pre-treating fed blood, and a main filter for treating blood pre-treated by the pre-treatment filter, wherein the pre-treatment filter is a laminate of first non-woven fabrics having a mean fiber diameter of 5 to 30 μm and a mean pore size of 10 to 30 μm, the main filter is a laminate of second non-woven fabrics having a mean fiber diameter of 1 to 5 μm, a mean pore size of 5 to 10 μm and a mean pore size distribution rate of 30% or more, a filling density of the pre-treatment filter with respect to a target blood throughput of the blood filter is 0.1 g/100 ml to 1 g/100 ml, and a filling density of the main filter with respect to a target blood throughput of the blood filter is 1 g/100 ml to 3 g/100 ml.

Each of the first and second non-woven fabrics may include polyethylene terephthalate or polybutylene terephthalate.

In another aspect of the present invention, provided is a method of manufacturing a blood filter including producing first melt-blown non-woven fabrics having a mean fiber diameter of 5 to 30 μm and a mean pore size of 10 to 30 μm, laminating the first melt-blown non-woven fabrics to produce a pre-treatment filter, producing second melt-blown non-woven fabrics having a mean fiber diameter of 1 to 5 μm, a mean pore size of 5 to 10 μm and a mean pore size distribution rate of 30% or more, laminating the second melt-blown non-woven fabrics to produce a main filter, and mounting the pre-treatment filter and the main filter in a case, wherein the first melt-blown non-woven fabrics are laminated such that a filling density of the pre-treatment filter with respect to a target blood throughput of the blood filter is 0.1 g/100 ml to 1 g/100 ml, and the second melt-blown non-woven fabrics are laminated such that a filling density of the main filter with respect to a target blood throughput of the blood filter is 1 g/100 ml to 3 g/100 ml.

The producing the first melt-blown non-woven fabrics may include melting polyethylene terephthalate or polybutylene terephthalate to prepare a first dope, spinning the first dope through a first die to form first fibers, and collecting the first fibers on a first collector, wherein a distance from the first die to the first collector (die to collector distance) is 200 mm or more.

The producing the second melt-blown non-woven fabrics may include melting polyethylene terephthalate or polybutyleneterephthalate to prepare a second dope, spinning the second dope through a second die to form second fibers, and collecting the second fibers on a second collector, wherein the spinning the second dope includes discharging the second dope through a nozzle of the second die, and spraying air to the second dope immediately before discharge through the nozzle, wherein a distance from the second die to the second collector is 60 mm or less, and an angle between the nozzle and the air is 60° or less.

Both the aforementioned general disclosure and the following Best Mode are provided only for illustration and description of the present invention and it should be understood that these are given for more detailed description of the inventions defined in the claims.

Advantageous Effects

According to the present invention, the blood filter includes a pre-treatment filter and a main filter and, at the same time, the mean pore size distribution rate of the main filter is controlled to be 30% or more, thereby realizing excellent leukocyte removal performance using a minimal porous material.

In addition, by realizing excellent leukocyte removal performance with a minimal porous material, blood throughput per unit time and erythrocyte recovery rates can be remarkably improved.

BRIEF DESCRIPTION OF THE DRAWINGS

The attached drawings are given for a better understanding of the present invention and constitute a part of the disclosure, which aim to illustrate the embodiments of the present invention and describe the principles of the present invention in conjunction with the following detailed description, in which:

FIG. 1 is a graph showing a pore size distribution of a main filter according to an embodiment of the present invention.

MODE FOR INVENTION

Now, embodiments of the present invention will be described in detail with reference to the annexed drawings. These embodiments are provided only for illustration to aid in a better understanding of the present invention and should not be construed as limiting the scope of the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims. Therefore, the present invention covers all of inventions defined in claims as well as modifications and alterations that fall into the scope of equivalents thereto.

The blood filter of the present invention includes a pre-treatment filter and a main filter.

The pre-treatment filter is a laminate of first non-woven fabrics and conducts pre-treatment to remove microaggregates, which may be formed by agglutination of blood cells occurring during transport or storage of blood, from blood fed to the blood filter.

The main filter is a laminate of second non-woven fabrics and removes leukocytes from blood from which microaggregates have been removed by the pre-treatment filter.

The first and second non-woven fabrics which have a three-dimensional network structure in which continuous or discontinuous fibers made of polyethylene terephthalate (PET) or polybutylene terephthalate (PBT) entangle with one another can be produced by a melt-blown method. The first and second non-woven fabrics can have a wide surface area and exhibit excellent filtration efficiency owing to small fiber diameter.

According to the present invention, the first non-woven fabric has a mean fiber diameter of 5 to 30 μm and a mean pore size of 10 to 30 μm.

When the mean fiber diameter of the first non-woven fabric is less than 5 μm, since the fiber has a low strength and flexibility, the non-woven fabric is pressed during filtration of blood by free fall, the gap between adjacent fibers becomes narrow, pressure loss is increased and filtration time can thus be significantly lengthened. On the other hand, when the mean fiber diameter of the first non-woven fabric exceeds 30 μm, the surface area of fibers filled for filtration is decreased and a chance of bringing fibers in contact with blood cells is reduced so that it may be difficult to efficiently filter blood cells.

When the mean pore size of the first non-woven fabric is less than 10 μm, microaggregates containing leukocytes cannot pass through the first non-woven fabric. For this reason, the blood cells are excessively collected in the first non-woven fabric, thus leading to a problem of shortened filtration lifespan. On the other hand, when the mean pore size of the first non-woven fabric exceeds 30 μm, blood cells directly reach the second non-woven fabric without selective filtration of microaggregates including leukocytes. As a result, filtration time may be unlimitedly increased due to shortened lifespan of the second non-woven fabric.

Meanwhile, in an embodiment of the present invention, the filling density of the pre-treatment filter with respect to the target blood throughput of the blood filter is 0.1 to 1 g/100 ml, preferably 0.11 to 0.15 g/100 ml. By setting the filling density of the pre-treatment filter blood filter within this range depending on the target blood throughput, microaggregates formed by agglutination of blood cells can be effectively removed and as a result, clogging of the main filter can be prevented.

When the filling density of the pre-treatment filter is less than 0.1 g/100 ml, microaggregates, which may be formed due to blood agglutination occurring during transport or storage of blood, pass through the pre-treatment filter and then reach the main filter having a relatively small mean pore size. As a result, the microaggregates suppress flow of blood, significantly reducing a filtration rate and even causing filter clogging. On the other hand, when the filling density of the pre-treatment filter exceeds 1 g/100 ml, the case of the blood filter may become unnecessarily large and excessively press the main filter, thus decreasing a mean pore size. As a result, a problem of deteriorated filtration speed may occur.

According to the present invention, the second non-woven fabric has a mean fiber diameter of 1 to 5 μm and a mean pore size of 5 to 10 μm.

When the mean fiber diameter of the second non-woven fabric constituting the main filter is less than 1 μm, pressure loss is increased during filtration of blood, cutting and fuzziness of fibers may occur due to weak strength of fibers. The cut fibers are contained in blood, thus causing transfusion side-effects. On the other hand, when the mean fiber diameter of the second non-woven fabric exceeds 5 μm, a chance of bringing fibers in contact with leukocytes is decreased and the leukocyte removal rate of the non-woven fabric web is thus deteriorated.

When the mean pore size of the second non-woven fabric is less than 5 μm, erythrocytes having a size of 6 to 8 μm cannot smoothly pass through the main filter, leading to increased pressure loss, significantly deteriorated blood treatment rate and even clogging. On the other hand, when the mean pore size of the second non-woven fabric exceeds 10 μm, leukocytes having a size of 12 to 25 μm easily pass through the leukocyte, thus reducing leukocyte removal rate of the blood filter.

In addition, the second non-woven fabric has a maximum pore size of 10 to 30 µm, preferably 10 to 15 µm, thereby allowing for selective adsorption of only leukocytes thereon, while allowing erythrocytes and platelets to pass through the same.

In addition, according to the present invention, the second non-woven fabric has a mean pore size distribution rate of 30% or more, preferably 45% or more. The term "mean pore size distribution rate" used herein refers a distribution rate of a range to which the mean pore size belongs in a pore size distribution graph measured from a capillary flow porometer (Model name: CFP-1100-AEL) produced by PMI, which indicates a degree of pore size uniformity of pores of non-woven fabrics.

The second non-woven fabric has a mean pore size distribution rate of 30% or more, thereby securing excellent leukocyte elimination performance while minimizing filling density of the main filter with respect to the target blood throughput of the blood filter. According to an embodiment of the present invention, the filling density of the main filter with respect to the target blood throughput of the blood filter is 1 to 3 g/100 ml, preferably 1 to 2 g/100 ml.

Meanwhile, fibers of the first and second non-woven fabrics preferably have a coefficient of diameter variation of 30 CV % or less. The coefficient of diameter variation is a percentage of the standard deviation of the mean fiber diameter. The coefficient of diameter variation of 30 CV % or less can secure uniform blood flow throughout the first and second non-woven fabrics. As a result, superior filtration efficiency and filtration performance can be uniformly exerted.

According to the present invention, blood treatment is conducted by first filtration through the pre-treatment filter and second filtration through the main filter. In this case, by controlling the mean pore size and mean pore size distribution rate of the filter used for each filtration, leukocytes can be effectively removed using differences in size between platelets, erythrocytes and leukocytes.

In addition, by controlling the filling amount of the porous material of the filter used for each filtration depending on the target blood throughput of the blood filter, time required for filtration can be minimized, erythrocyte recovery rates can be increased and unnecessary stress of erythrocyte can be reduced so that hematocytolysis rates can be minimized.

Hereinafter, a method of manufacturing a blood filter according to an embodiment of the present invention will be described in detail.

The method of the present invention includes: producing first melt-blown non-woven fabrics; laminating the first melt-blown non-woven fabrics to produce a pre-treatment filter; producing second melt-blown non-woven fabrics; laminating the second melt-blown non-woven fabrics to produce a main filter; and mounting the pre-treatment filter and the main filter in a case.

As described above, the first melt-blown non-woven fabrics have a mean fiber diameter of 5 to 30 µm and a mean pore size of 10 to 30 µm.

The producing the first melt-blown non-woven fabrics includes melting polyethylene terephthalate or polybutylene terephthalate to prepare a first dope, spinning the first dope through a first die to form first fibers, and collecting the first fibers on a first collector. In this case, the distance from the first die to the first collector (die to collector distance: DCD) may be 200 mm or more.

The spinning the first dope may include discharging the first dope through a nozzle of the first die and spraying high-temperature high-pressure air to the second dope immediately before discharge through the nozzle. In this case, the angle between the nozzle and the air may be 30 to 120° and is preferably 45 to 60° so as to uniformly control the mean fiber diameter and the mean pore size.

Subsequently, the pre-treatment filter is produced by laminating the first melt-blown non-woven fabrics such that the filling density of the pre-treatment filter with respect to the target blood throughput of the blood filter is 0.1 to 1 g/100 ml.

The second melt-blown non-woven fabrics have a mean fiber diameter of 1 to 5 µm, a mean pore size of 5 to 10 µm and a mean pore size distribution rate of 30% or more.

The producing the second melt-blown non-woven fabrics may include melting polyethylene terephthalate or polybutylene terephthalate to prepare a second dope, spinning the second dope through a second die to form second fibers, and collecting the second fibers on a second collector. In this case, the distance from the second die to the second collector (DCD) may be 60 mm or less.

The spinning the second dope may include discharging the second dope through a nozzle of the second die, and spraying high-temperature high-pressure air to the second dope immediately before discharge through the nozzle. In this case, the angle between the nozzle and the air may be 60° or less.

Subsequently, the main filter is produced by laminating the second melt-blown non-woven fabrics such that the filling density of the pre-treatment filter with respect to the target blood throughput of the blood filter is 1 to 3 g/100 ml.

After mounting the pre-treatment filter and main filter thus produced in a case, sealing is conducted using an ultrasonic welding machine in order to prevent blood leakage, thereby completing the blood filter of the present invention. Selectively, the blood filter may be sterilized at a temperature of 100 to 120° C. and a pressure of 1 to 1.2 kgf/cm$^2$ for 20 minutes to 1 hour.

Hereinafter, the spinning steps of the first and second dopes will be described in more detail.

As described above, the spinning of the dopes includes discharging the dope through the nozzle of the die, and spraying high-temperature high-pressure air to the dope immediately before discharge through the nozzle. According to an embodiment of the present invention, the spinning is carried out at 230 to 300° C., and the high-temperature high-pressure air has a pressure of 0.5 to 2 kgf/cm$^2$.

When the spinning temperature is less than 230° C., the fibers cannot be sufficiently drawn due to excessively low spinning temperature. As a result, it is impossible to obtain non-woven fabrics having a mean fiber diameter of 30 µm or less and it is difficult to satisfy required filter performance due to decreased bonding strength between fibers collected on the collector. On the other hand, when the spinning temperature exceeds 300° C., strength between fibers collected on the collector becomes excessively strong due to excessively high temperature. As a result, it is impossible to form pores having an appropriate pore size and texture similar to paper may occur. Accordingly, the subsequent process may not proceed efficiently.

As the spinning temperature increases within the range of 230 to 300° C., the drawing of fibers is facilitated and the mean fiber diameter of the non-woven fabric is thus decreased. Hence, according to an embodiment of the present invention, the spinning temperature applied to produce the second melt-blown non-woven fabrics for the main filter may be set to be higher than the spinning temperature applied to produce the first melt-blown non-woven fabrics for the pre-treatment filter.

Meanwhile, when the pressure of the air is lower than 0.5 kgf/cm², the fibers cannot be sufficiently drawn, thus making it impossible to obtain non-woven fabrics having a mean fiber diameter of 30 μm or less. On the other hand, when the pressure of the compression gas exceeds 2 kgf/cm², fibers may be blown off and it is difficult to produce non-woven fabrics suitable for production of the blood filter due to creation of excessive fuzzy fibers.

As the pressure of the air increases within the range of 0.5 to 2 kgf/cm², the drawing of fibers is facilitated and the mean fiber diameter of the non-woven fabrics is thus decreased. Hence, according to an embodiment of the present invention, the pressure of the air applied to produce the second melt-blown non-woven fabrics for the main filter may be set to be higher than the pressure of the air applied to produce the first melt-blown non-woven fabrics for the pre-treatment filter.

In general, as DCD increases, the movement distance of high-temperature high-pressure air and spun fibers increases, the lamination uniformity ratio of fibers decreases and non-uniformity of the mean pore size thus increases. Thus, according to an embodiment of the present invention, DCD used to produce the first melt-blown non-woven fabrics for the pre-treatment filter is 200 mm or more, while DCD used to produce the second melt-blown non-woven fabrics for the main filter is 60 mm or less.

According to an embodiment of the present invention, the angle between the nozzle for discharging the dope and the high-temperature high-pressure air in the spinning step is set to 45 to 60°.

When the angle is less than 45°, the angle of the nozzle is small, thus making it difficult to implement mass-production and management due to serious damage by impact during attachment and removal of the nozzle. Moreover, the fibers of the spun non-woven fabric orient in only one direction, making it difficult to control the mean pore size and causing a problem of lengthened filtration time due to increased pressure during filtration. On the other hand, when the angle exceeds 60°, the fibers spun from the nozzle and the high-temperature high-pressure air create turbulence, thus leading to a serious problem in controlling the mean pore size.

Meanwhile, by suitably controlling the spinning temperature, air pressure, DCD, angle between the nozzle and air and so on, the weight and mean thickness of the non-woven fabric can be controlled. According to an embodiment of the present invention, the first melt-blown non-woven fabrics for the pre-treatment filter have a weight of 30 to 70 g/m² and a mean thickness of 0.15 to 0.40 mm, and the second melt-blown non-woven fabrics for the main filter have a weight of 10 to 40 g/m² and a mean thickness of 0.08 to 0.20 mm.

Meanwhile, according to an embodiment of the present invention, by treating the second non-woven fabric alone, or both the first and second non-woven fabrics, with a blood affinity agent containing a polymer having a non-ionic hydrophilic group, a critical wetting surface tension (CWST) of 63 to 120 dyne/cm, preferably 80 to 110 dyne/cm can be imparted to the non-woven fabrics.

The CWST can be obtained by dropping droplets of a liquid having a surface tension varying from 2 to 4 dyne/cm (mN/m) on the surface of a sample and then checking absorbed drops and non-absorbed drops while observing the liquid droplets. CWST, represented in dyne/cm, is defined by an average of the surface tension of the absorbed liquid and surface tension of the non-absorbed liquid. A liquid having a lower surface tension than the CWST of the non-woven fabric spontaneously soaks the non-woven fabric when coming in contact with the non-woven fabric web. For example, a non-woven fabric having lower CWST than water having a surface tension of 72 dyne/cm does not wet with water when contacting water. Accordingly, the CWST of the non-woven fabric may be considered an indicator of hydrophilicity and, as the CWST increases, the hydrophilicity of the non-woven fabric also increases.

When the affinity of the non-woven fabric to blood is excessively weak, blood treatment time becomes excessively long, which is impractical. On the other hand, when affinity to blood is excessively strong, leukocytes as well as erythrocytes and platelets can be adsorbed thereon and then removed. When the CWST of the non-woven fabric is lower than 63, affinity to blood becomes excessively weak, blood may coagulate due to excessively lengthened blood treatment time, and when blood passes through pores of the non-woven fabric web, collision between erythrocytes and fibers increases, and LDH (lactate dehydrogenase), an indicator of erythrocyte damage, increases. As a result, erythrocyte lifespan may be rapidly shortened. On the other hand, when the CWST of the non-woven fabric exceeds 120, as the fabric adsorbs erythrocytes and platelets, a blood preparation containing ingredients in degrees required in the art cannot be obtained.

In particular, a polybutylene terephthalate (PBT) non-woven fabric has an advantage of maintaining pore physical properties during sterilization due to excellent heat resistance, but cannot have CWST satisfying the range defined above due to low hydrophobicity. Accordingly, the PBT non-woven fabric should be treated with a blood affinity agent containing a polymer having a non-ionic hydrophilic group. The polymer having a non-ionic hydrophilic group is, for example, 2-hydroxyethylmethacrylate, vinyl pyrrolidone or the like.

The blood filter of the present invention produced above has a high leukocyte removal rate of 99.99% or more and a high erythrocyte recovery rate of 85% or more. In particular, a time required for treating 250 to 350 ml of an erythrocyte concentrate, or 320 to 400 ml of whole blood with the blood filter of the present invention is 30 minutes or less, which means that the blood filter of the present invention can provide treatment of blood at a high filtration rate. Accordingly, the blood filter of the present invention can be used as a blood purification device during blood transfusion and donation requiring excellent leukocyte removal rate and erythrocyte recovery rate.

Hereinafter, the present invention will be described in more detail with reference to Examples and Comparative Examples. However, the following examples are provided only for a better understanding of the present invention and should be not construed as limiting the scope of the present invention.

Experimental Example 1: Measurement of Mean Fiber Diameter (μm) of Non-Woven Fabric The mean fiber diameter of the non-woven fabric was measured using a scanning electron microscope and an image analyzer (JVC Digital Camera KY-F70B in combination with Image-Pro Plus software). At this time, 20 samples were measured.

Experimental Example 2: Measurement of Mean Pore Size (μm) and Mean Pore Size Distribution Rate (%) of Non-Woven Fabric The mean pore size (μm) and mean pore size distribution rate (%) of the non-woven fabric were measured using a capillary flow porometer (PMI, CFL-1100-AE) in accordance with ASTM F 316-03. Specifically, a circular sample having a diameter of 1 inch was sufficiently soaked in Galwick solution having a surface tension of 15.9 dyne/cm and then fed to the equipment. At this time, 10 samples were measured.

Example 1

Polybutylene terephthalate having an intrinsic viscosity of 0.52 and a melting point of 224° C. was melted at 250° C. to prepare a spinning solution, and first non-woven fabrics for the pre-treatment filter and second non-woven fabrics for the main filter were produced under different process conditions using an ordinary melt-blown non-woven fabric manufacturing device.

Specifically, first non-woven fabrics having a mean fiber diameter of 11 μm, a mean pore size of 24.1 μm, a weight of 35 g/m² and a mean thickness of 0.31 mm were produced while controlling the dope discharge amount and air temperature under conditions of an air pressure of 0.7 kgf/cm² and a DCD of 250 mm.

In addition, second non-woven fabrics having a mean fiber diameter of 1.3 μm, a mean pore size of 7.95 μm, a weight of 25 g/m² and a mean thickness of 0.14 mm were produced while controlling the dope discharge amount and air temperature under conditions of an air pressure of 1.2 kgf/cm², a DCD of 50 mm and the angle between the nozzle and air of 60°. The mean pore size distribution rate of the second non-woven fabrics was 57%, as shown in FIG. 1. Subsequently, the first and second non-woven fabrics were coated with a blood affinity agent (hydroxyethylmethacrylate (HEMA) available from Daejung Co., Ltd.).

Subsequently, the first and second non-woven fabrics were cut so as to have a filtration area of 32 cm².

The cut first non-woven fabrics were laminated to produce 1.716 g of a pre-treatment filter, the cut second non-woven fabrics were laminated to produce 5.412 g of a main filter, and the pre-treatment filter and the main filter were mounted in a case made of polycarbonate and sealed using an ultrasonic welding machine to produce a blood filter having a target blood throughput of 330 ml.

That is, the filling density of the pre-treatment filter with respect to the target blood throughput of the blood filter was 0.52 g/100 ml and the filling density of the main filter with respect to the target blood throughput of the blood filter was 1.64 g/100 ml.

Subsequently, the blood filter was sterilized at a temperature of 115° C. and a pressure of 1.15 kgf/cm² for 30 minutes to complete a blood filter.

Example 2

A blood filter was completed in the same manner as in Example 1, except that the filling density of the main filter with regard to the target blood throughput of the blood filter was 1.22 g/100 ml.

Example 3

A blood filter was completed in the same manner as in Example 1, except that second non-woven fabrics having a mean pore size of 8.01 μm and a mean pore size distribution rate of 40% were produced using a DCD of 60 mm, and the filling density of the pre-treatment filter with regard to the target blood throughput of the blood filter was 0.44 g/100 ml.

Example 4

A blood filter was completed in the same manner as in Example 3, except that the filling density of the main filter with regard to the target blood throughput of the blood filter was 1.22 g/100 ml.

Example 5

A blood filter was completed in the same manner as in Example 1, except that the filling density of the pre-treatment filter with regard to the target blood throughput of the blood filter was 0.14 g/100 ml.

Comparative Example 1

A blood filter was completed in the same manner as in Example 1, except that the filling density of the main filter with regard to the target blood throughput of the blood filter was 0.98 g/100 ml.

Comparative Example 2

A blood filter was completed in the same manner as in Example 3, except that the filling density of the pre-treatment filter with regard to the target blood throughput of the blood filter was 0.09 g/100 ml.

Comparative Example 3

A blood filter was completed in the same manner as in Example 1, except that second non-woven fabrics having a mean fiber diameter of 1.3 μm, a mean pore size of 8.25 μm, a weight of 25 g/m², a mean thickness of 0.14 mm and a mean pore size distribution rate of 28% were produced by setting the angle between the nozzle and air to 120° during production of the second non-woven fabrics and controlling the dope discharge amount and air temperature at an air pressure of 1.2 kgf/cm² and a DCD of 80 mm.

The filtration time, erythrocyte recovery rate, residual leukocytes and filtration performance of the blood filters obtained by Examples and Comparative Examples mentioned above were measured using the following methods.

Filtration Time (min)

Filtration time was obtained by measuring a time for 310 to 350 ml of an erythrocyte blood preparation (average 330 ml) containing SAG-M (saline, adenine, glucose, mannitol: 88.9 ml) used to lengthen a retention period of blood to pass through the filter and then be filtered.

Erythrocyte Recovery Rate (%)

Erythrocyte recovery rate (%) was obtained by loading a blood filter in a 2 m-height stand, directly connecting the blood filter to a tube through which whole blood passes, filtering blood, and collecting 15 cc of blood before and after filtration. The number of blood cells was quantitatively measured using an automated hematology analyzer (SYSMEX, XP-300) under the conditions shown in Table 1 below to obtain an erythrocyte recovery rate. Detailed calculation is given in Equation 1 below.

$$\text{Erythrocyte recovery rate (\%)} = \frac{\text{Blood volume after filtration} \times \text{Hct \% after filtration}}{\text{Blood volume before filtration} \times \text{Hct \% before filtration}} \quad \text{Equation 1}$$

TABLE 1

| Items | Auto CBC Reference |
|---|---|
| RBC Counter | 3.80~6.5 M/μl |
| WBC Counter | 4.0~11.0 K/μl |
| WBC differential counter | Lym-: 20~45%, Neutro-: 40~75% |
| Hemoglobin (Hb) | 11.5~18 g/dL |
| Hematocrit (Hct) | 37.0~50.0% |
| Platelet | 150~400 K/μl |

The Number of Residual Leukocytes after Filtration ($1\times10^6$/Unit)

The number of residual leukocytes was measured using a LeucoCOUNT Kit which is a bead-based flow cytometry method. 100 μl of blood was fed to a TruCOUNT tube containing a predetermined number of beads, 400 μl of a LeucoCOUNT reagent containing RNAse, a detergent and propidium iodide (PI) was then fed to the TruCOUNT tube, and these ingredients were reacted at room temperature in a dark room for 5 minutes. The number of beads (R1) and the number of leukocytes (R2) were measured using FACS (BD bioscience, San Jose, Calif., USA) and the number of residual leukocytes after filtration was calculated in accordance with the following Equation 2.

$$\text{Number of residual leukocytes } (1 \times 10^6/\text{unit}) = \frac{\text{Number of leukocytes } (R2)}{\text{Number of beads } (R1)} \times \frac{\text{Total bead number}}{\text{Amount of blood}} \quad \text{Equation 2}$$

Filtration Performance

Filtration performance of the blood filters was evaluated on a four-point scale (⊚: excellent, ○: good, Δ: medium, x: poor) in consideration of all elements measured by the aforementioned methods.

Filtration time, erythrocyte recovery rate, the number of residual leukocytes and filtration performance of blood filters measured by the aforementioned methods are shown in the following Table 2.

TABLE 2

| | Filling density of filter with target blood throughput of blood filter (g/100 ml) | | Main filter | | | | | |
|---|---|---|---|---|---|---|---|---|
| | Pre-treatment filter | Main filter | Mean pore size (μm) | Mean pore size distribution on rate (%) | Filtration time (min) | Erythrocyte recovery rate (%) | Number of residual leukocytes ($1 \times 10^6$/unit) | Filtration performance |
| Ex. 1 | 0.52 | 1.64 | 7.95 | 57 | 9.7 | 91.7 | 0 | ⊚ |
| Ex. 2 | 0.52 | 1.22 | 7.95 | 57 | 14.5 | 89.0 | 0.03 | ⊚ |
| Ex. 3 | 0.44 | 1.64 | 8.01 | 40 | 22.6 | 93.4 | 0 | ⊚ |
| Ex. 4 | 0.44 | 1.22 | 8.01 | 40 | 24.3 | 90.8 | 0.03 | ⊚ |
| Ex. 5 | 0.14 | 1.64 | 7.95 | 57 | 28.0 | 87.6 | 0 | ○ |
| Comp. Ex. 1 | 0.52 | 0.98 | 7.95 | 57 | 120 or more | 87.6 | 3.34 | x |
| Comp. Ex. 2 | 0.09 | 1.64 | 8.01 | 40 | 120 or more | 66.9 | 0 | x |
| Comp. Ex. 3 | 0.52 | 1.64 | 8.25 | 28 | 21.6 | 95.0 | 1.43 | x |

The invention claimed is:

1. A method of manufacturing a blood filter, the method comprising:

producing first melt-blown non-woven fabrics having a mean fiber diameter of 5 to 30 μm and a mean pore size of 10 to 30 μm;

laminating the first melt-blown non-woven fabrics to produce a pre-treatment filter;

producing second melt-blown non-woven fabrics having a mean fiber diameter of 1 to 5 μm, a mean pore size of 5 to 10 μm and a mean pore size distribution rate of 30% or more;

laminating the second melt-blown non-woven fabrics to produce a main filter; and mounting the pre-treatment filter and the main filter in a case, wherein the first melt-blown non-woven fabrics are laminated such that a filling density of the pre-treatment filter with respect to a target blood throughput of the blood filter is 0.1 g/100 ml to 1 g/100 ml, and the second melt-blown non-woven fabrics are laminated such that a filling density of the main filter with respect to the target blood throughput of the blood filter is 1 g/100 ml to 3 g/100 ml.

2. The method according to claim 1, wherein the producing of the first melt-blown non-woven fabrics comprises:

melting polyethylene terephthalate or polybutylene terephthalate to prepare a first dope;

spinning the first dope through a first die to form first fibers; and collecting the first fibers on a first collector, wherein a distance from the first die to the first collector is 200 mm or more.

3. The method according to claim 2, wherein the producing of the second melt-blown non-woven fabrics comprises:

melting polyethylene terephthalate or polybutylene terephthalate to prepare a second dope;

spinning the second dope through a second die to form second fibers; and collecting the second fibers on a second collector, wherein the spinning of the second dope comprises:

discharging the second dope through a nozzle of the second die; and spraying air to the second dope before discharging through the nozzle, wherein a distance from the second die to the second collector is 60 mm or less, and an angle between the nozzle and the air is 60° or less.

* * * * *